United States Patent [19]

Honda et al.

[11] Patent Number: 4,534,798
[45] Date of Patent: Aug. 13, 1985

[54] COMPOSITION FOR PARTITIONING BLOOD COMPONENTS

[75] Inventors: Seiichirou Honda, Takarazuka; Hiroshi Ogawara, Ohtsu; Mutsumi Fukuda, Osaka, all of Japan

[73] Assignee: Sekisui Kagaku Kogyo Kabushiki Kaisha, Osaka, Japan

[21] Appl. No.: 553,187

[22] Filed: Nov. 18, 1983

Related U.S. Application Data

[62] Division of Ser. No. 292,029, Aug. 11, 1981, Pat. No. 4,457,782.

[30] Foreign Application Priority Data

Aug. 18, 1980 [JP] Japan ................................. 55-113811
Aug. 28, 1980 [JP] Japan ................................. 55-119397
May 29, 1981 [JP] Japan ................................. 56-83050

[51] Int. Cl.$^3$ ........................ C08L 91/00; B01D 12/00
[52] U.S. Cl. .................................... 106/266; 106/901; 210/510.1; 210/927; 252/315.1
[58] Field of Search ............... 252/60, 315.1; 106/266; 210/927

[56] References Cited

U.S. PATENT DOCUMENTS

| 3,780,935 | 12/1973 | Likacs | 210/65 |
| 3,852,194 | 12/1974 | Zine | 210/83 |
| 4,021,340 | 5/1977 | Zine | 210/515 |
| 4,101,422 | 7/1978 | Lamont | 210/515 |
| 4,172,803 | 10/1979 | Toshizi | 210/259 |
| 4,457,782 | 7/1984 | Honda | 106/266 |

FOREIGN PATENT DOCUMENTS 2743882 3/1978 Fed. Rep. of Germany .
1542165 3/1979 United Kingdom .

Primary Examiner—Theodore Morris
Attorney, Agent, or Firm—Wenderoth, Lind & Ponack

[57] ABSTRACT

A blood-partitioning composition comprising a mixture of
  (1) a thixotropy-imparting agent,
  (2) a first viscous liquid material having strong interaction with the thixotropy-imparting agent, and
  (3) a second viscous liquid material having no strong interaction with the thixotropy-imparting agent and having good compatibility with the first viscous liquid material,
said composition having a specific gravity at 20° C. of from 1.03 to 1.08, and use of the composition in a method for partitioning a sample of blood.

6 Claims, No Drawings

COMPOSITION FOR PARTITIONING BLOOD COMPONENTS

This is a division of application Ser. No. 292,029, filed Aug. 11, 1981, now U.S. Pat. No. 4,457,782.

This invention relates to a composition for partitioning blood components, and more specifically to a novel composition for separating a relatively light normally liquid blood phase containing serum or plasma from a relatively heavy normally solid blood phase containing erythrocytes, leukocytes, platelets, etc. by subjecting a sample of blood to centrifugation.

In recent years, diagnostic testing of blood components in clinical laboratories has become very important and the number of cases subjected to such testing has been increasing. Many of biochemical tests involve use of blood serum or plasma as a sample, and as a preparatory procedure for examination, it is necessary to separate blood serum or plasma from solid blood components such as erythrocytes and leukocytes. It is the conventional practice to sample blood serum or plasma by centrifuging whole blood thereby to sediment a blood cell portion, and siphoning the supernatant liquid by a pipette. This method, however, results in insufficient separation of the serum or plasma portion and is very time-consuming. Various methods have therefore been suggested recently to perform this separating operation with simplicity in high yields.

One of such prior methods suggested comprises adding to a sample of blood a substance having a specific gravity intermediate between serum or plasma and a solid blood component, and positioning this substance intermediate between the two types of blood components by centrifugation thereby forming a partitioning wall between them. Although this method enables serum or plasma to be separated only by decantation and permits saving of both time and labor, it is not without defects.

Such partitioning wall-forming materials so far proposed are available in the form of a solid, a liquid or a mixture of these (see, for example, U.S. Pat. Nos. 3,780,935 and 3,852,194).

Solid materials include, for example, a powdery or pelletized material of polystyrene. When this material is used, its function as a partitioning wall is insufficient, and the blood cells may get mixed with the serum or plasma. Or the partitioning wall itself is susceptible to destruction.

Acrylic polymers are known as the liquid partition-forming material. Production of a highly viscous liquid polymer, such as the acrylic polymers, from monomers generally gives rise to difficult problems such as the removal of impurities depending upon the control of the reaction and the method of performing the reaction. In addition, the liquid material has the defect of poor adaptability for transportation and storage before use because it has flowability.

Known solid-liquid mixtures include thixotropic compositions such as a mixture of a silicone and silica powder and a mixture of modified liquid polybutadiene and alumina. They have the defect that their viscosity generally increases or decreases with the lapse of time. When the viscosity of such a composition increases, a strong centrifugal force is required for a long period of time for moving the composition to an intermediate position between the serum or plasma and a blood cell portion by centrifugation after it has been stored for a long period of time in the bottom of a container. Sometimes, such a composition does not become flowable even when subjected to a centrifugal force of 500 to 2,000 G which is usually employed in hospital and biomedical laboratories. Conversely, when the viscosity of the composition decreases with time, the composition has a decreased viscosity after storage for a long time in a container. If the stored composition is centrifuged together with a sample of blood in a container and the container is inclined for pouring off the serum, the partitioning wall of the composition will collapse and the blood cells will get mixed with the serum.

It is an object of this invention therefore to provide a composition for partitioning a sample of blood, which is free from the aforesaid defects and does not substantially change in viscosity with the lapse of time.

Another object of this invention is to provide a composition for partitioning a sample of blood, which can easily form a stable partitioning wall under normal centrifuging conditions and permits very simple and accurate separation of the serum or plasma portion.

Still another object of this invention is to provide a composition for partitioning a sample of blood, which can be transported and stored simply without any particular attention or device.

A further object of this invention is to provide use of such partitioning composition for the partitioning of a sample of blood.

Other objects and advantages of this invention will become apparent from the following description.

According to this invention, there is provided a composition for partitioning a sample of blood, said composition comprises a mixture of (1) a thixotropy-imparting agent,
(2) a first viscous liquid material having strong interaction with the thixotropy-imparting agent, and
(3) a second viscous liquid material having no strong interaction with the thixotropy-imparting agent and having good compatibility with the first viscous liquid material, said composition having a specific gravity at 20° C. of from 1.03 to 1.08.

The blood partitioning composition provided by this invention will now be described in detail.

Thixotropy-imparting agent

Since the composition of this invention serves to form a partitioning wall in an interface between the serum or plasma phase and the solid phase (including erythrocytes, leukocytes, platelets, etc.) separated by centrifugation, it is necessary to stabilize the partitioning wall in order to avoid re-mixing of the serum or plasma with the solid components after separation. For example, the partitioning wall must be stabilized against flowing and collapsing during transportation of a container containing the composition of this invention and a sample of blood after the separating operation, or during inclining of the container for separation of the serum or plasma. It is for this purpose that the thixotropy-imparting agent is used.

In the present specification and the appended claims, the term "thixotropy-imparting agent" denotes a solid powder, particularly an inorganic solid powder, which can impart thixotropy to a mixture of the first and second viscous liquid materials.

Such a solid powder has an average particle diameter of generally 1 to 1,000 millimicrons, preferably 1 to 100 millimicrons, especially preferably 5 to 30 millimicrons, a specific surface area of generally at least 10 m²/g, preferably 50 to 500 m²/g, especially preferably 100 to 400 m²/g, and a specific gravity of generally 1.5 to 30, preferably 1.8 to 2.5, and most suitably 2.0 to 2.4. Desirably, the solid powder is substantially insoluble in water.

Examples of the inorganic solid powder capable of imparting thixotropy in accordance with this invention include powders of silica, alumina, glass, talc, kaolin, bentonite, titania, zirconium, asbestos and carbon black.

If desired, these solid powders may be subjected to a surface hydrophilizing or hydrophobizing treatment, for example a grafting reaction using a grafting agent such as a combination of a vinylsilane compound and a vinyl monomer, or a coupling reaction using a coupling agent such as a silane coupling agent (e.g., γ-chloropropyltrimethoxysilane or γ-glycidoxypropyltrimethoxysilane).

These solid powders may be used singly or as a mixture of two or more.

Among these thixotropy-imparting agents, fine silica powder is most suitable in this invention. The fine silica powder may, if desired, be hydrophobized at its surface by coupling reaction with dimethyldichlorosilane.

First viscous liquid material

The first viscous liquid material used to prepare the composition of this invention by mixing with the thixotropy-imparting agent is a viscous liquid material having strong interaction with the thixotropy-imparting agent.

The expression "having strong interaction with the thixotropy-imparting agent", as used in the present specification and the appended claims, means that when a certain thixotropy-imparting agent and a certain viscous liquid material are mixed and dispersed uniformly and then centrifuged for 30 minutes at a rotating speed of 4,000 rpm by a centrifugal separator having an arm length of 10 cm, no localization is seen in the distribution of the components of the above mixture. The localization of the distribution is evaluated in the following manner. Specifically, analysis samples are collected at several different points of the mixed mass after the centrifugal separation, and weighed. Then, the thixotropy-imparting agent dispersed in the samples is separated and weighed to determine the amount of the thixotropy-imparting agent per unit of the samples. When the differences in the amount of the thixotropy-imparting agent among the samples is within ±20%, it is judged that there is no localization in the distribution.

The first viscous liquid material having strong interaction with the thixotropy-imparting agent (inorganic solid powder) may generally be a substantially a water-insoluble natural material or a synthetic polymeric material which is liquid at room temperature (about 5° to about 30° C.) and contains a hydrophilic functional group in the molecule, particularly a carbonyl group (which may be present in the form of a carboxyl group, an ester linkage, an amide linkage and/or a ketone linkage), or an epoxy group. The amount of the carbonyl groups or epoxy groups is not critical, and can be varied depending upon the type of the thixotropy-imparting agent to be mixed, for example. The carbonyl groups can exist in a carbonyl equivalent of generally 80 to 300, preferably 100 to 200, and the epoxy groups can exist in an epoxy equivalent of generally 100 to 1,000, preferably 200 to 500. The "carbonyl equivalent" and "epoxy equivalent" respectively mean the number of grams of a resin containing 1 gram-equivalent of carbonyl or epoxy groups.

Specific examples of the first viscous liquid material are given below.

(1) Acrylic oligomers such as homo- or copolymers of a low degree of polymerization having a number average molecular weight of 500 to 10,000 derived from acrylic acid esters, methacrylic acid esters, maleic acid esters, etc.

(2) Polyester oligomers such as a copolymer of a dicarboxylic acid and a diol which has a number average molecular weight of 500 to 10,000.

(3) Acid-modified liquid synthetic polymeric materials, such as a maleinized product of a liquid rubbery polymer such as liquid polybutadiene and liquid polyisoprene, which has a number average molecular weight of 500 to 10,000.

(4) Animal and vegetable oils, such as soybean oil, linseed oil, safflower oil, and fish oils.

(5) Liquid epoxy resins, such as a condensation product of bisphenol A and epichlorohydrin, which have an epoxy equivalent of 150 to 500 and a molecular weight of 300 to 500.

(6) Epoxy-modified liquid synthetic polymeric materials, such as an epoxidized product of liquid 1,2-polybutadiene or liquid 1,4-polybutadiene which has an epoxy equivalent of 150 to 1,000 and a number average molecular weight of 1,000 to 5,000.

(7) Epoxy-modified products of animal and vegetable oils such as epoxidized soybean oil, epoxidized linseed oil and epoxidized safflower oil.

Among these first viscous liquid materials, the epoxy-modified liquid synthetic polymeric materials and epoxidized animal and vegetable oils are especially preferred.

The first viscous liquid material used in this invention is a liquid epoxidized animal or vegetable oil or a synthetic polymeric material containing carbonyl or epoxy groups, said liquid being viscous at room temperature, and desirably has a viscosity, measured at 20° C., of generally at least 200 cps, preferably 300 to 30,000 cps, more preferably 350 to 10,000 cps. Conveniently, it has a specific gravity at 20° C. of generally 0.9 to 1.2, preferably 1.0 to 1.1, more preferably 1.02 to 1.08.

Examples of the first viscous liquid material which can be especially advantageously used in this invention are epoxidized soybean oil having a viscosity at 20° C. of 300 to 700 cps and a specific gravity of 20° C. of 0.95 to 1.00, and epoxidized products of liquid 1,2-polybutadiene and liquid 1,4-polybutadiene which have an epoxy equivalent of 150 to 250 and a number average molecular weight of 3,000 to 5,000.

Second viscous liquid materials

The second viscous liquid material used in combination with the first viscous liquid material in accordance with this invention is a viscous liquid material having no strong interaction with the thixotropy-imparting agent. Thus, the second viscous liquid material is such that when it is mixed with the thixotropy-imparting agent and uniformly dispersed and centrifuged for 30 minutes at a rotating speed of 4,000 rpm by a centrifugal separator having an arm length of 10 cm, localization occurs in the distribution of the thixotropy-imparting agent in the mixture.

Although the second viscous liquid material has no strong interaction with the thixotropy-imparting agent to be mixed, it should have good compatibility with the first viscous liquid material.

In the present specification and appended claims, the expression that "the second viscous material has good compatibility with the first viscous liquid material" means that when the first viscous liquid material and the second viscous liquid material are uniformly mixed and the mixture was allowed to stand for 1 week at room temperature, no phase separation perceptible to the naked dye occurs.

The second viscous liquid material having the above properties is a high-molecular-weight material which is composed substantially only of carbon and hydrogen and is liquid at room temperature, and a high-molecular-weight material which is composed substantially of carbon, hydrogen and chlorine and is liquid at room temperature. Specific examples are given below.

(1) Liquid chlorinated paraffins which have a number average molecular weight of 300 to 600 and a chlorine content of 5 to 40% by weight.

(2) Liquid polyolefins, for example polybutene having a number average molecular weight of 300 to 1,500 polyisoprene having a number average molecular weight of 10,000 to 50,000, and polybutadiene having a number average molecular weight of 1,000 to 3,000. These polyolefins may contain hydroxyl, epoxy or carbonyl groups at the ends in order to increase their compatibility with the first viscous liquid material.

(3) Chlorinated products of the materials described in (2) above. These chlorinated products desirably have a chlorine content of generally 5 to 40% by weight, preferably 7 to 20% by weight. A chlorinated product of polybutene having a number average molecular weight of 600 and a chlorine content of 20% by weight is preferred.

These materials may be used singly or as a mixture of two or more.

Advantageously, the above second viscous liquid materials used in accordance with this invention which are viscous at room temperature and have a viscosity measured at 20° C. of at least 1,000 cps, preferably 6,000 to 150,000 cps, more preferably 10,000 to 30,000 cps. Desirably, they have a specific gravity at 20° C. of generally 0.85 to 1.20, preferably 0.95 to 1.10, more preferably 1.00 to 1.08.

Especially advantageously used as the second viscous liquid material in this invention is chlorinated polybutene having a number average molecular weight of 400 to 1,500 having a chlorine content of 7 to 20% by weight.

Water-insoluble amines

The composition of this invention comprising a mixture of the aforesaid thixotropy-imparting agent, first viscous liquid material and second viscous liquid material may, if desired, further contain a substantially water-insoluble amine. Inclusion of the amine can lead to a marked improvement in the stability of the viscosity of the composition with the lapse of time. The expression "substantially water-insoluble" means that the solubility in water is not more than 0.1% at 20° C.

The substantially water-insoluble amine used for the above purpose is conveniently compatible with the first or second viscous liquid material, and has a molecular weight of generally 100 to 500, preferably 150 to 400. Especially suitable amines are of the following general formula

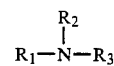

wherein $R_1$, $R_2$ and $R_3$ each represent a hydrogen atom or an alkyl group, provided that at least one of $R_1$, $R_2$ and $R_3$ is a higher alkyl group having at least 8 carbon atoms, preferably 12 to 20 carbon atoms, which alkyl group may be mono-substituted with a polyoxyalkylene group such as a polyoxyethylene or polyoxypropylene group. Specific examples of the amine are dodecylamine, tetradecylamine, hexadecylamine, octadecylamine, dodecyldimethylamine, tetradecyldimethylamine, octadecyldimethylamine, polyoxyethyleneoctadecylamine, and trioctylamine.

These amines may be used singly or as a mixture of two or more.

Among the above amines, octadecyldimethylamine and trioctylamine are especially suitable.

Other additives

The composition in accordance with this invention may, if desired, further contain substantially water-insoluble coloring agents, titanium oxide and zinc oxide, etc. in addition to the aforesaid components.

Preparation of the composition of this invention

The composition of this invention can be prepared by intimately mixing the individual components described hereinabove. The order of addition of these components is not at all restricted. For example, all of the components may be mixed simultaneously. Or the mixing may be performed in a multiplicity of steps. For example, two selected components are first mixed, and then the remaining components are added and mixed either sequentially or at once; or vice versa. Generally, it is convenient to first mix the first viscous liquid material and the second viscous liquid material, and then simultaneously, or successively in an optional order, mix the thixotropy-imparting agent and if desired, the water-insoluble amine and other additives.

The proportions of the individual components vary depending upon the types of the thixotropy-imparting agent, the first viscous liquid material and/or second viscous liquid material, etc. Generally, the thixotropy-imparting agent can be used in an amount of 2 to 30 parts by weight, preferably 3 to 15 parts by weight, more preferably 4 to 8 parts by weight, per 100 parts by weight of the first and second viscous liquid materials combined. The ratio between the first viscous liquid material and the second viscous liquid material varies depending upon the degree of interaction between each of these viscous liquid materials and the thixotropy-imparting agent. Generally, it is convenient to use 20 to 600 parts by weight, preferably 30 to 500 parts by weight, more preferably 50 to 450 parts by weight, of the second viscous liquid material per 100 parts by weight of the first viscous liquid material.

The amount of the water-insoluble amine to be used optionally is neither restricted strictly, and can be varied depending upon the types of the other components, etc. Generally, the suitable amount of the water-insoluble amine is 0.001 to 0.1 part by weight, preferably 0.005 to 0.09 part by weight, more preferably 0.01 to 0.05 part by weight, per part by weight of the thixotropy-imparting agent. The amounts of the other additives are small depending upon their types, and are usually not more than 5.0% by weight based on the weight of the entire composition.

Since the composition in accordance with this invention is used to form a partitioning wall between the serum or plasma phase and the solid blood phase by a centrifugal action, it should have a specific gravity intermediate between the two phases. Thus, the composition should have a specific gravity in a standard condition at 20° C. of 1.03 to 1.08, preferably 1.04 to 1.06.

Accordingly, in preparing the composition of this invention, the mixing proportions of the individual components should be selected within the above range such that the specific gravity of the resulting composition at 20° C. comes within the aforesaid range.

The mixing of the individual components can be performed in a customary manner by using a mixing device, such as a three-roll mill or a planetary mixer, generally at room temperature and in some cases at an elevated temperature of up to about 100° C.

The composition of this invention prepared as above is a thixotropic composition having a specific gravity at 20° C. of 1.03 to 1.08, preferably 1.04 to 1.06, a viscosity at a shear speed of 1 $sec^{-1}$ of 60,000 to 400,000 cps, preferably 100,000 to 250,000 cps, and a thixotropy coefficient of generally at least 1.8, preferably 2.0 to 4.0.

The term "thixotropy coefficient", as used herein, denotes a value calculated in accordance with the following equation.

$$\text{Thixotropy coefficient} = \frac{\text{Viscosity (cps) at a shear speed of sec}^{-1}}{\text{Viscosity (cps) at a shear speed of 10 sec}^{-1}}$$

The composition of this invention for partitioning of a sample of blood has such moderate thixotropy and shows no increase in viscosity with time as is demonstrated by working examples given hereinbelow. Hence, not only immediately after production but also after storage for long periods of time, no specially strong centrifugal force is required, but a partitioning wall of the composition is formed easily within a blood collection tube under normal centrifuging conditions (at a rotating speed of 1,500 to 3,500 rpm) so that serum or plasma can be separated with simplicity and good accuracy. Furthermore, since the viscosity of the composition of this invention does not decrease with time, it can stably form a partitioning wall even when used after storage for a long period of time. Once the partitioning wall has been formed, it will not collapse even when after the lapse of a long period of time, the blood drawing tube is inclined. In this way, the composition of this invention has many advantages over conventional products used for the same purpose.

In separating the blood components by using the composition of this invention, no particular attention should be paid, and any known method (for example, the method described in the above-cited U.S. Patent specifications) can be used. For example, a certain fixed amount of the composition of this invention is put in a container, and a sample of blood drawn from the subject is added. The mixture is then centrifuged for about 2 to about 20 minutes at a rotating speed of 1,500 to 3,500 rpm. As a result, a partitioning wall of the composition of this invention is formed in the interface between the serum or plasma and the solid phase containing erythrocytes, etc. Thus, the serum or plasma can be separated and taken out simply with good accuracy by such an operation as decantation.

The following Examples further illustrate the present invention.

The specific gravities, viscosities, specific surface areas and thixotropy coefficients used in these examples are all measured at 20° C. The viscosities are measured at a shearing speed of 1 $sec^{-1}$.

EXAMPLE 1

(A) Silica powder having an average particle diameter of 10 millimicrons, a specific surface area of 200 $m^2/g$ and a specific gravity of 2.2 as a thixotropy-imparting agent, epoxidized soybean oil having a specific gravity of 1.00, a viscosity of 420 cps and an epoxy equivalent of 200 as a first viscous liquid material and liquid chlorinated polybutene having a specific gravity of 1.00, a viscosity of 8,000 cps and a chlorine content of 14% by weight as a second viscous liquid material were provided.

(B) Using these components, the three mixtures shown in Table 1 each consisting of two components were prepared. The mixtures a and b were each put in a glass container and centrifuged at a rotating speed of 4,000 rpm for 30 minutes using a centrifugal separator having an arm length of 10 cm. Immediately after the centrifugation, the tube was maintained perpendicular, and the state of the mixture therein was observed.

TABLE 1

| Mixture | Silica powder (parts by weight) | Epoxidized soybean oil (parts by weight) | Liquid chlorinated polybutene (parts by weight) |
|---------|---------------------------------|------------------------------------------|-------------------------------------------------|
| a       | 1                               | 10                                       | —                                               |
| b       | 1                               | —                                        | 10                                              |
| c       | —                               | 3                                        | 2                                               |

In the mixture a, silica was uniformly dispersed in the epoxidized soybean oil, but silica in the mixture b was localized below the liquid chlorinated polybutadiene. On the other hand, when the mixture c was allowed to stand at room temperature for 1 week in a container. It was found that the epoxidized soybean oil and the liquid chlorinated polybutene were uniformly dissolved in each other, and no phase separation occurred.

(C) The silica powder, epoxidized soybeans oil and the liquid chlorinated polybutene in this order were weighed in a weight ratio of 1:3:7. In a vacuum vessel kept at 50° C., the epoxidized soybean oil and the liquid chlorinated polybutene were mixed with stirring, the silica powder was added and dispersed uniformly. The mixture was cooled to 20° C. to give a blood partitioning composition having a specific gravity of 1.05. The composition had a viscosity at 1 $sec^{-1}$ of 200,000 centipoises and a thixotropy coefficient of 3.0.

One gram of the composition was introduced into each of four 10 ml glass tubes. Immediately after production, a sample of blood was added to one of these tubes, and centrifuged at a rotating speed of 2,000 rpm for 3 minutes with an arm length of 10 cm. The composition formed a partitioning wall between the serum and the blood clot, and the serum could be easily separated and collected by decantation.

Another tube was turned upside down, and inclined at an angle of about 60 degrees to the horizontal plane. However, the composition in it did not flow.

The remaining two tubes were left to stand at room temperature, and after one month, subjected to the same tests as above. There was no increase or decrease in the viscosity of the composition, and the same test results as above were obtained.

The tube in which the partitioning wall was formed as a result of centrifugal separation effected immediately after the production of the composition was again inclined, but the partitioning wall did not collapse.

COMPARATIVE EXAMPLE 1

The same silica powder, epoxidized soybean oil and liquid chlorinated polybutene as used in Example 1 were provided.

One part by weight of the silica powder was added to 10 parts by weight of the epoxidized soybean oil, and the mixture was heated with stirring to form a mixture d having a specific gravity of 1.05. Separately, 1 part by weight of the silica powder was added to 6 parts by weight of the liquid chlorinated polybutene, and the mixture was heated with stirring to give a mixture e having a specific gravity of 1.05.

A sample of blood was added to the mixture d in a tube, and centrifuged under the same conditions as in Example 1. Immediately after the production of the mixture d, a partitioning wall of the mixture was formed in an intermediate position in the whole blood. One month later, its viscosity became so high that the composition became immovable and no partitioning wall was formed.

The mixture e was subjected to the same inverting test as in Example 1. Both immediately after the production and after one month from then, the mixture e was seen to flow downward slowly.

EXAMPLE 2

Amorphous hydrophilic silica powder having a specific gravity of 2.2, a specific surface area of 200 $m^2/g$ and an average particle diameter of 10 millimicrons as a thixotropy-imparting agent, epoxidized soybean oil having a specific gravity of 1.0, a viscosity of 1,700 cps and an epxoy equivalent of 200 as a first viscous liquid material, and liquid chlorinated polybutene having a specific gravity of 1.05, a viscosity of 50,000 cps and a chlorine content of 20% by weight as a second viscous liquid material were provided.

The fine silica powder, epoxidized soybean oil and liquid chlorinated polybutene were weighed in a weight ratio of 1:8:2 in this order, and in a vacuum vessel at 50° C., the epoxidized soybean oil and the liquid chlorinated polybutene were mixed with stirring, and then the fine silica powder was added and dispersed uniformly to give a blood partitioning composition having a specific gravity of 1.06. The mixture had a viscosity of 1 $sec^{-1}$ of 150,000 centipoises and a thixotropy coefficient of 2.5.

One gram of the composition was introduced into each of 10 ml glass tubes. Immediately after preparation of the composition, a sample of blood was added to one of these tubes, and after coagulation of the blood, centrifuged at a rotating speed of 2,500 rpm for 3 minutes with an arm length of 10 cm. As a result, the composition formed a partitioning wall between the serum and the blood cell portion, and the serum could be easily separated and collected by decantation.

Samples of blood withdrawn from subjects were biochemicaly tested for 32 items including proteins, lipids, serum enzymes, inorganic ions, etc. in the absence or presence of the resulting composition as a serum separating material. The serum test values were then compared. Substantially the same results were obtained, and the use of this serum separating material does not at all affect the serum test values.

On the other hand, another tube containing the composition alone was turned upside down, and inclined at an angle of about 60° with respect to the horizontal plate. However, the composition did not flow.

Furthermore, the composition was stored at room temperature for 30 days, and then subjected to the same biochemical tests and inverting test as above. The results were the same. Specifically, there was no increase or decrease in the viscosity of the composition, and a partitioning wall of the composition was formed easily. The results of biochemical testing of the serum appeared to be the same as those obtained by using the composition immediately after its preparation. The serum separating composition did not flow even when the tube was inverted at 60°.

The tube in which the partitioning wall was formed as a result of the centrifugal separation effected immediately after the preparation of the above composition was again inclined 30 days later. But the partitioning wall did not collapse.

COMPARATIVE EXAMPLE 2

One part by weight of the same fine silica powder as used in Example 2 and 9 parts by weight of 2-ethylhexyl acrylate oligomer having a specific viscosity of 1.0 and a viscosity of 100,000 were mixed uniformly to give a composition. Samples of the serum were obtained under the same conditions as in Example 2 using the composition immediately after production as a serum separating agent, and were biochemically tested for the same items as in Example 2. The results were compared with the serum test values of samples of serum collected by centrifuging the blood without using the aforesaid separating agent and collecting the serum by a pipette. Clear differences were seen in two items regarding proteins and two items regarding lipid.

The composition was stored at room temperature for 30 minutes, and then introduced into a glass tube. Furthermore, a sample of blood was added and centrifuged at a rotating speed of 2,500 rpm using a centrifugal separator having an arm length of 10 cm. However, the composition did not move, and in order to form a partitioning wall intermediate between the serum and the blood cell portion, a period of 10 minutes at 4,000 rpm was required.

EXAMPLE 3

Nine parts by weight of silica powder having an average particle diameter of 10 millimicrons, a specific surface area of 200 $m^2/g$ and a specific gravity of 2.2 as a thixotropy-imparting agent, 70 parts by weight of liquid chlorinated polybutene having a specific gravity of 1.02 and a viscosity of 1,000 cps as a second liquid viscous liquid material, 21 parts by weight of epoxidized soybean oil having a specific gravity of 1.0, a viscosity of 1,700 cps and an epoxy equivalent of 200 as a first viscous liquid material, and 0.2 part by weight of octylamine were kneaded on a three-roll mill to give a blood partitioning composition having a specific gravity of 1.06. The composition had a viscosity at 1 $sec^{-1}$ of 180,000 and a thixotropy coefficient of 2.0.

The composition was then introduced in an amount of 1 g into a 10 ml glass tube. A sample of blood was added, and after the coagulation of the blood, centrifuged for 3 minutes at a rotating speed of 2,500 rpm (1160 G). The composition formed a partitioning wall intermediate between the serum and blood clot. The tube was inclined in order to separate the serum. The serum could be collected without collapsing of the partitioning wall. The same inverting test as in Example 1 was carried out, but the composition did not flow.

Furthermore, the composition was stored at 40° C. for 30 days, and the same test as above was carried out. No effect on the formation of the partitioning wall was noted, and in the inverting test, the composition did not flow. Thus, the composition was found to have very good stability with time.

EXAMPLE 4

Six parts by weight of silica powder having a particle diameter of 16 millimicrons, a specific surface area of 130 m²/g and a specific gravity of 2.2 as a thixotropy-imparting agent, 17 parts of epoxidized soybean oil having a specific gravity of 1.00 and a viscosity of 410 cps as a first viscous liquid material, 77 parts of a second viscous liquid chlorinated polybutene having a specific viscosity of 1.02 and a viscosity of 9,000 cps as a second viscous liquid material, and 0.2 part by weight of octadecyldimethylamine were kneaded on a three-roll mill to give a blood partitioning composition having a specific gravity of 1.05, a viscosity of 150,000 cps and a thixotropy coefficient of 2.2.

One gram of the composition was poured into each of 10 ml glass tubes. Then, a sample of blood was added, and after coagulation of the blood, was centrifuged at a rotating speed of 2,500 rpm for 10 minutes with arm length of 10 cm. As a result, a partitioning wall was formed intermediate between the serum and the blood cell portion. The serum could be easily separated and collected by decantation.

Samples of blood withdrawn from subjects were biochemically tested for 32 items including proteins, lipids, serum enzymes, inorganic ions, etc. in the absence or presence of the resulting composition as a serum partitioning agent. The serum test valves were then compared, and substantially the same results were obtained. The use of this serum separating agent did not affect the serum test values.

On the other hand, a glas tube containing this serum separating agent was turned upside down and inclined at an angle to 60° with respect to the horizontal plane. The composition did not flow. When the composition was stored at 40° C. for 2 months and then subjected to the same test as above, quite the same results were obtained. Specifically, a stable partitioning wall was formed by centrifugation at 2,500 rpm for 10 minutes. There was no effect on the serum test values, and the composition did not flow in the inverting test.

EXAMPLE 5

Four parts by weight of silica powder having an average particle diameter of 7 millimicrons, a specific surface area of 300 m²/g and a specific gravity of 2.2 as a thixotropy-imparting agent, 80 parts by weight of polybutyl acrylate oligomer having a specific gravity of 1.0 and a viscosity of 8,000 centipoises as a first viscous liquid material, 16 parts by weight of liquid chloroprene having a specific gravity of 1.20 and a viscosity of 50,000 cps as a second viscous liquid material, and 0.5 part of trioctylamine were kneaded by a planetary mixer to give a blood partitioning composition having a specific gravity of 1.05 and a viscosity of 200,000 cps and a thixotropy coefficient of 2.0. This composition had the equivalent performances to the composition obtained in Example 4, and showed quite the same performances after it was stored for 2 months at 40° C.

EXAMPLE 6

Five parts by weight of hydrophobic silica powder having an average particle diameter of 16 millimicrons, a specific surface area of 110 m²/g and a specific gravity of 2.2 as a thixotropy-imparting agent, 25 parts by weight of epoxidized 1,2-polybutadiene having a specific gravity of 0.99 and a viscosity of 50,000 cps as a second viscous liquid material, 70 parts by weight of chlorinate polybutene having a specific gravity of 1.05 and a viscosity of 30,000 cps as a second viscous liquid material, and 0.1 part by weight of dodecyldimethylamine were kneaded by a planetary mixer to give a blood partitioning composition having a specific gravity of 1.06, a viscosity of 160,000 cps and a thixotropy coefficient of 2.1. The composition had the same performance as in Example 4.

EXAMPLE 7

Five parts by weight of hydrophobic silica powder having a particle diameter of 16 microns, a specific surface area of 110 m²/g and a specific gravity of 2.2 as a thixotropy-imparting agent, 30 parts by weight of a 50:50 mixture (viscosity 4,500 cps; specific gravity 1.0) of epoxidized soybean oil having a viscosity of 410 cps and a specific gravity of 1.0 and polybutyl acrylate oligomer having a viscosity of 8,000 cps and a specific gravity of 1.0 as a first viscous liquid material, 65 parts by weight of chlorinated polybutene having a viscosity of 23,000 cps and a specific viscosity of 1.03 as a second viscous liquid substance and 0.5 part of triocytlamine were kneaded on a three-roll mill to give a blood-partitioning composition having a specific gravity of 1.05, a viscosity of 150,000 cps and a thixotropy coefficient of 2.3. The composition had the same performances as in Example 4.

What we claim is:

1. A blood-partitioning composition consisting essentially of a mixture of
   (1) a thixotropy-imparting agent which is an inorganic solid powder having an average particle diameter of from 1 to 1,000 millimicrons, a specific surface area of at least 10 m²/g and a specific gravity in the range of from 1.5 to 3.0;
   (2) a first viscous liquid material having strong interaction with the thixotropy-imparting agent such that when the thixotropy-imparting agent is uniformly dispersed with the first viscous liquid and then centrifuged, no localization of said thixotropic agent occurs in the centrifuged liquid, said first viscous liquid having a viscosity at 20° C. of at least 200 centripoises and a specific gravity at 20° of from 0.9 to 1.2, said first material being a natural animal or vegetable oil modified with epoxy groups or a synthetic polymeric material containing carbonyl or epoxy groups in the molecule, and wherein said first material is liquid at room temperature;
   (3) a second viscous liquid material having no strong interaction with the thixotropy-imparting agent such that when the thixotropy-imparting agent is uniformly dispersed with the second viscous liquid material and then centrifuged, the thixotropy-imparting agent is localized in said second viscous liquid, said second viscous liquid having good compatibility with the first viscous liquid material such that no substantial phase separation occurs upon mixing the two liquids, said second liquid material having a viscosity at 20° C. of at least 1,000 centipoises and a specific gravity at 20° C. of 0.85 to 1.20 and being a high-molecular-weight material liquid at room temperature composed substantially only of carbon and hydrogen or a high-molecular-weight material liquid at room temperature composed substantially of carbon, hydrogen and chlorine; and (4) (a) at least one water-insoluble amine(;) of the following formula:

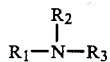

wherein $R_1$, $R_2$ and $R_3$ each represent a hydrogen atom or an alkyl group, provided that at least one of $R_1$, $R_2$ and $R_3$ is a higher alkyl group containing at least 8 carbon atoms, which alkyl group may be substituted with one polyoxyalkylene group;

said composition having a specific gravity at 20° C. of from 1.03 to 1.08, a viscosity at a shearing speed of 1 sec$^{-1}$ of from 60,000 to 400,000 centipoises and a thixotropy coefficient of at least 1.8, the amount of said thixotropy-imparting agent being from 2 to 30 parts by weight per 100 parts by the combined weight of the first and second viscous liquid material, and the amount of said second viscous liquid material being from 20 to 600 parts by weight per 100 parts by weight of the first viscous liquid material.

2. The composition of claim 1 wherein the water-insoluble amine is selected from the group consisting of dodecylamine, tetradecylamine, hexadecylamine, octadecylamine, dodecyldimethylamine, tetradecyldimethylamine, octadecyldimethylamine, polyoxyethyleneoctadecylamine and trioctylamine.

3. The composition of claim 1 wherein the amount of the water-insoluble amine is from 0.001 to 0.1 part by weight per part by weight of the thixotropy-imparting agent.

4. The composition of claim 1 wherein said first viscous liquid material is epoxidized soybean oil.

5. The composition of claim 1 wherein at least one of $R_1$, $R_2$ and $R_3$ is a higher alkyl group containing at 12 to 20 carbon atoms.

6. The composition of claim 1, wherein the amine has a molecular weight of 100 to 500.

* * * * *